US012599438B2

(12) United States Patent
Auvray et al.

(10) Patent No.: US 12,599,438 B2
(45) Date of Patent: Apr. 14, 2026

(54) DETERMINING END POINT LOCATIONS FOR A STENT

(71) Applicant: KONINKLIJKE PHILIPS N.V., Eindhoven (NL)

(72) Inventors: Vincent Maurice André Auvray, Meudon (FR); Stéphane Allaire, Nanterre (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 228 days.

(21) Appl. No.: 18/286,398

(22) PCT Filed: Apr. 6, 2022

(86) PCT No.: PCT/EP2022/059104
§ 371 (c)(1),
(2) Date: Oct. 11, 2023

(87) PCT Pub. No.: WO2022/218774
PCT Pub. Date: Oct. 20, 2022

(65) Prior Publication Data
US 2024/0197405 A1     Jun. 20, 2024

(30) Foreign Application Priority Data

Apr. 16, 2021     (EP) .................................... 21290021

(51) Int. Cl.
A61B 34/20          (2016.01)
A61B 6/00          (2006.01)
(Continued)

(52) U.S. Cl.
CPC ................ A61B 34/20 (2016.02); A61B 6/12 (2013.01); A61B 6/463 (2013.01); A61B 6/469 (2013.01);
(Continued)

(58) Field of Classification Search
CPC ......... A61B 6/469; A61B 6/463; A61B 6/504; A61B 6/5247; G06T 2207/10016; G06T 2207/20101; G06T 2207/30101
See application file for complete search history.

(56) References Cited

U.S. PATENT DOCUMENTS

2011/0071404 A1* 3/2011 Schmitt .............. A61B 5/02007
382/128
2016/0022208 A1    1/2016 Gopinath
(Continued)

OTHER PUBLICATIONS

International Search Report and Written Opinion of PCT/EP2022/059104, dated Jul. 21, 2022.

*Primary Examiner* — Gerald Johnson

(57)          ABSTRACT

A system (100) for determining a suitability of positions along a lumen (110) as end point locations for a stent, includes one or more processors (120) configured to: receive (S110), from an intraluminal imaging device (130), a temporal sequence of intraluminal images ($140_1 \ldots n$) representing positions along the lumen (110), including at least a first intraluminal image ($140_{i \subset 1 \ldots n}$); and identify (S120), whether or not the first intraluminal image ($140_{i \subset 1 \ldots n}$) represents a suitable end point location for the stent.

19 Claims, 4 Drawing Sheets

(51) Int. Cl.

| | |
|---|---|
| *A61B 6/12* | (2006.01) |
| *A61B 6/46* | (2024.01) |
| *A61B 6/50* | (2024.01) |
| *A61B 8/12* | (2006.01) |
| *G06T 7/00* | (2017.01) |
| *G06T 7/11* | (2017.01) |
| *G06T 7/33* | (2017.01) |
| *G06T 7/60* | (2017.01) |

(52) U.S. Cl.

CPC .............. *A61B 6/486* (2013.01); *A61B 6/504* (2013.01); *A61B 6/5247* (2013.01); *A61B 8/12* (2013.01); *G06T 7/0016* (2013.01); *G06T 7/11* (2017.01); *G06T 7/337* (2017.01); *G06T 7/60* (2013.01); *A61B 6/4441* (2013.01); *A61B 2034/2065* (2016.02); *G06T 2207/10016* (2013.01); *G06T 2207/10116* (2013.01); *G06T 2207/20101* (2013.01); *G06T 2207/30101* (2013.01); *G06T 2207/30204* (2013.01)

(56) References Cited

U.S. PATENT DOCUMENTS

| | | |
|---|---|---|
| 2018/0085170 A1 | 3/2018 | Gopinath |
| 2019/0015056 A1 | 1/2019 | Sata |
| 2019/0282182 A1 | 9/2019 | Scott |
| 2020/0000420 A1 | 1/2020 | Sakaguchi |

* cited by examiner

100

240

250

130

260

120

S110

S120

S130

S140

S150

S160

$140_u$

230 — Compressed

DETERMINING END POINT LOCATIONS FOR A STENT

CROSS-REFERENCE TO PRIOR APPLICATIONS

This application is the U.S. National Phase application under 35 U.S.C. § 371 of International Application No. PCT/EP2022/059104, filed on Apr. 6, 2022, which claims the benefit of European Patent Application No. 21290021.1, filed on Apr. 16, 2021. These applications are hereby incorporated by reference herein.

TECHNICAL FIELD

The present disclosure relates to determining a suitability of positions along a lumen as end point locations for a stent. A system, a computer-implemented method, and a related computer program product, are disclosed.

BACKGROUND

In the medical field, stents are routinely inserted into vascular, coronary, biliary, bronchial, urinary, and other lumens within the anatomy in order to keep the relevant passageway open. The need, and ultimate location for a stent, is determined by a physician, often under the guidance of an intraluminal imaging device.

By way of an example, a deep venous intervention typically begins with the generation of an initial venogram of the patient's vasculature using contrast-enhanced X-ray imaging. A guidewire is then inserted into the vasculature under X-ray imaging, and an intraluminal imaging device such as an intravascular ultrasound "IVUS" imaging catheter, or an optical coherence tomography "OCT" imaging catheter, is translated along the guidewire in a "pullback" procedure in order to image, and thereby diagnose portions of a lumen within the vasculature. Narrowings, or "compressions", or "thromboses" in the lumen that restrict blood flow, are often indicative of vascular disease, whereas more open regions of the lumen where the blood flow is less restricted typically indicate healthy regions. If a stent is deemed necessary, for example, if the lumen is compressed by more than 50% with respect to a reference healthy region, the physician may determine a suitable location, or "landing zone" for the stent from the IVUS images by identifying diseased, and healthy regions of the lumen. The physician may also identify branches, also known as "confluences" in the lumen from the IVUS images. In a vascular procedure, the physician will typically specify the stent's landing zone such that the stent overlaps a diseased region and the ends of the stent are located in healthy regions, and preferably avoiding that the stent overlaps any confluences. In order to do this, the physician typically uses the IVUS images that were generated during the pullback procedure. The physician may also use information from additional IVUS images that are obtained by re-visiting potential sites of interest, additional X-ray images that are generated contemporaneously with the IVUS images, and the initial venogram. However, this process can be laborious due to the complexity of analysing the IVUS images, and the complexity of relating the information from the different imaging systems.

Having specified the stent's landing zone, the physician typically measures a length of the landing zone in order to specify a length of a stent for insertion into the lumen. In a vascular procedure, the length of the landing zone is typically specified by positioning the IVUS imaging catheter such that the fiducial markers that are arranged along the shaft of the IVUS imaging catheter, overlap the intended landing zone. An additional clinician supporting the physician then manually counts the number of fiducial markers within the landing zone on an X-ray image. The physician then specifies a stent length based on the count. However, this procedure is inefficient and error-prone because of the need for the additional clinician, the need to position the IVUS imaging catheter such that its fiducial markers overlap the landing zone, and the need to manually count the fiducial markers to determine its length. Fiducial markers are typically disposed at coarse, one-centimetre, intervals along the axis of the IVUS imaging catheter, and there may be fifteen or more markers to count.

Similar challenges occur when specifying stents for insertion into other lumens within the anatomy, including coronary, biliary, bronchial, and urinary lumens. However there remains a need for solutions to one or more of these issues.

SUMMARY

According to one aspect of the present disclosure, a system for determining a suitability of positions along a lumen as end point locations for a stent, is provided. The system includes one or more processors configured to:

receive, from an intraluminal imaging device, a temporal sequence of intraluminal images representing positions along the lumen, including at least a first intraluminal image; and identify, whether or not the first intraluminal image represents a suitable end point location for the stent.

Further aspects, features, and advantages of the present disclosure will become apparent from the following description of examples, which is made with reference to the accompanying drawings.

DETAILED DESCRIPTION

Figure 1:
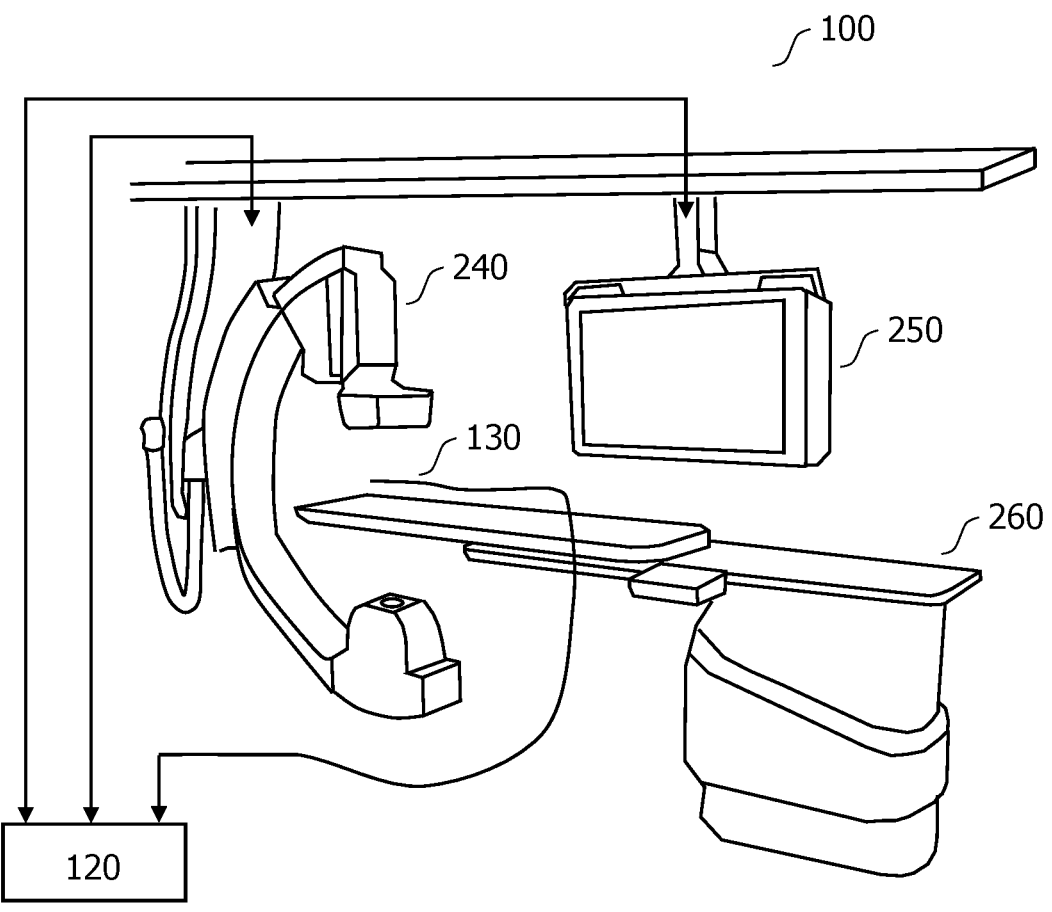
FIG. 1 is a schematic diagram illustrating an example of a system 100 for determining a suitability of positions along a lumen as end point locations for a stent, in accordance with some aspects of the disclosure.

Examples of the present disclosure are provided with reference to the following description and figures. In this description, for the purposes of explanation, numerous specific details of certain examples are set forth. Reference in the specification to "an example", "an implementation" or similar language means that a feature, structure, or characteristic described in connection with the example is included in at least that one example. It is also to be appreciated that features described in relation to one example may also be used in another example, and that all features are not necessarily duplicated in each example for the sake of brevity. For instance, reference is made to herein a system that includes one or more processors that are configured to carry out one or more methods. It is to be appreciated that the one or more methods, may alternatively be provided as a computer implemented method, or implemented in a computer program product, or provided on a computer-readable storage medium, in a corresponding manner.

In the following description, reference is made to a system that includes one or more processors configured to carry out various functions that may be steps of a method that involve determining a suitability of positions along a lumen as end point locations for a stent. Reference is made to a lumen in the form of a vein within the vasculature. However, it is to be appreciated that the methods described in this disclosure may, in a similar manner, be used to determine the suitability of positions along other lumens within the vasculature as end point locations for a stent, such as for example arteries. Moreover, it is to be appreciated that the methods may be used to determine the suitability of positions along lumens in general within the anatomy as end point locations for a stent, including lumens within the coronary, biliary, bronchial, urinary, and other regions of the anatomy.

In the methods described herein, reference is made to an intraluminal imaging device in the form of an IVUS imaging device. The IVUS imaging device may for example be provided in the form of an IVUS imaging catheter, an IVUS imaging guidewire, and so forth. However, it is to be appreciated that the IVUS imaging device serves only as an example of an intraluminal imaging device, and that the methods may as appropriate, be used with other types of intraluminal imaging devices, including an OCT imaging device, a TEE probe, and so forth.

In the methods described herein, reference is also made to the detection of an intraluminal imaging device in X-ray images. In this respect, it is to be appreciated that the X-ray images may be generated by various types of X-ray imaging systems. For example, the X-ray images may be generated by a planar imaging system that generates planar X-ray images, or a volumetric X-ray imaging system that generates volumetric X-ray images. Planar X-ray imaging systems typically include a support arm such as a so-called "C-arm", or an "O-arm", that supports an X-ray source-detector arrangement. Planar X-ray imaging systems may alternatively include a support arm with a different shape to these examples. Planar X-ray imaging systems typically generate planar X-ray images with the support arm held in a static position with respect to an imaging region during the acquisition of image data. By contrast, volumetric X-ray imaging systems typically generate image data whilst rotating, or stepping, an X-ray source-detector arrangement around an imaging region, and subsequently reconstruct the image data obtained from multiple rotational angles into volumetric image data. Examples of volumetric X-ray imaging systems include computed tomography "CT" imaging systems, cone beam CT "CBCT" imaging systems, and spectral CT imaging systems.

It is noted that the methods disclosed herein may be provided as a non-transitory computer-readable storage medium including computer-readable instructions stored thereon, which, when executed by at least one processor, cause the at least one processor to perform the method. In other words, the computer-implemented methods may be implemented in a computer program product. The computer program product can be provided by dedicated hardware, or hardware capable of running the software in association with appropriate software. When provided by a processor, the functions of the method features can be provided by a single dedicated processor, or by a single shared processor, or by a plurality of individual processors, some of which can be shared. The explicit use of the terms "processor" or "controller" should not be interpreted as exclusively referring to hardware capable of running software, and can implicitly include, but is not limited to, digital signal processor "DSP" hardware, read only memory "ROM" for storing software, random access memory "RAM", a non-volatile storage device, and the like. Furthermore, examples of the present disclosure can take the form of a computer program product accessible from a computer-usable storage medium, or a computer-readable storage medium, the computer program product providing program code for use by or in connection with a computer or any instruction execution system. For the purposes of this description, a computer-usable storage medium or a computer readable storage medium can be any apparatus that can comprise, store, communicate, propagate, or transport a program for use by or in connection with an instruction execution system, apparatus, or device. The medium can be an electronic, magnetic, optical, electromagnetic, infrared, or a semiconductor system or device or propagation medium. Examples of computer-readable media include semiconductor or solid state memories, magnetic tape, removable computer disks, random access memory "RAM", read-only memory "ROM", rigid magnetic disks and optical disks. Current examples of optical disks include compact disk-read only memory "CD-ROM", compact disk-read/write "CD-R/W", Blu-Ray™ and DVD.

As mentioned above, in the medical field it is often necessary to determine a suitable location, or "landing zone" for a stent within a lumen. In order to address this issue, the inventors have provided a system and a method of determining a suitability of positions along a lumen as end point locations for a stent. FIG. 1 is a schematic diagram illustrating an example of a system 100 for determining a suitability of positions along a lumen as end point locations for a stent, in accordance with some aspects of the disclosure. The system 100 includes one or more processors 120 that are configured to:

receive S110, from an intraluminal imaging device 130, a temporal sequence of intraluminal images $140_{1 \ldots n}$ representing positions along the lumen 110, including at least a first intraluminal image $140_{i \subset 1 \ldots n}$; and identify S120, whether or not the first intraluminal image $140_{i \subset 1 \ldots n}$ represents a suitable end point location for the stent.

As illustrated in FIG. 1, the system 100 may optionally also include one or more of: the intraluminal imaging device 130, an extra-body imaging system 240 such as the X-ray imaging system illustrated in FIG. 1, or alternatively another imaging system, one or more display devices 250, and a patient bed 260. The system 100 may optionally also include a user interface device such as a keyboard, and/or a pointing device such as a mouse (not illustrated in FIG. 1) for controlling execution of the method. The elements of the system are in communication with each other as illustrated by way of the interconnecting arrowed lines in FIG. 1. By way of an example, the intravascular imaging catheter may be an IVUS imaging catheter such as the Visions PV 0.014P RX available from Philips Healthcare, Best, The Netherlands.

Figure 2:
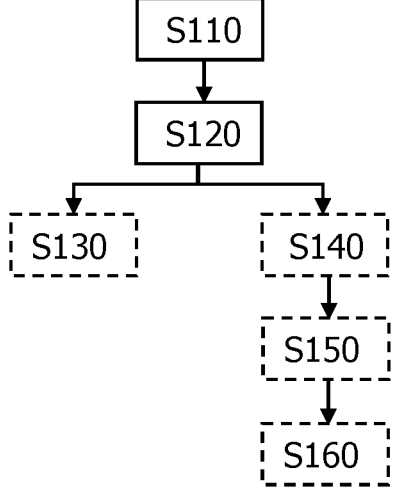
FIG. 2 is a flowchart illustrating an example of a method of determining a suitability of positions along a lumen as end point locations for a stent, in accordance with some aspects of the disclosure.

FIG. 2 is a flowchart illustrating an example of a method of determining a suitability of positions along a lumen as end point locations for a stent, in accordance with some aspects of the disclosure. The operations illustrated in FIG. 2 may be carried out by the one or more processors 120 of the system 100 illustrated in FIG. 1. The flowchart illustrated in FIG. 2 includes the receiving S110 operation, and the identifying S120 operation described above in relation to FIG. 1, and may optionally also include one or more of the operations S130, S140, S150 and S160, as described in more detail below.

Figure 3:
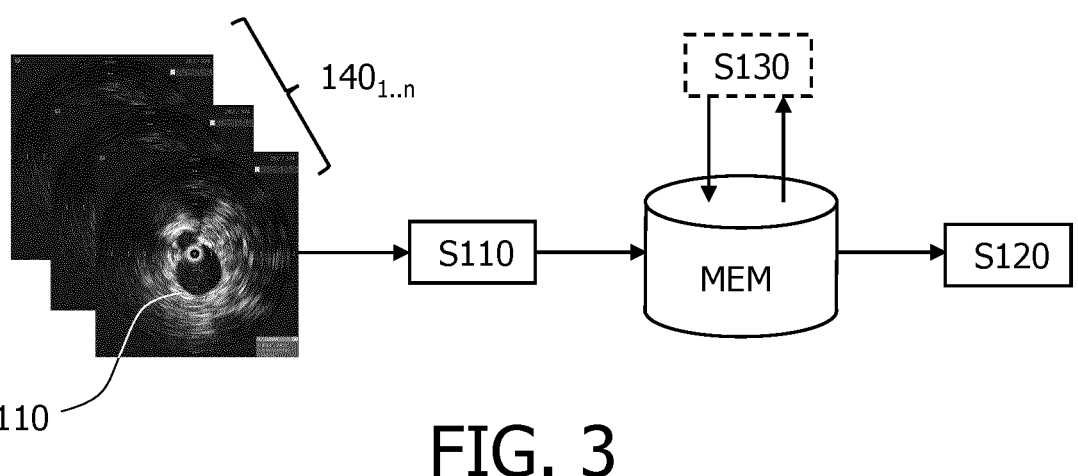
FIG. 3 is a schematic diagram illustrating an example of determining a suitability of positions along a lumen as end point locations for a stent, in accordance with some aspects of the disclosure.

FIG. 3 is a schematic diagram illustrating an example of determining a suitability of positions along a lumen as end point locations for a stent, in accordance with some aspects of the disclosure. FIG. 3 illustrates schematically the operations of receiving S110, and identifying S120, described above, and may optionally also include the operation S130 described in more detail below.

With reference to FIG. 1-FIG. 3, in the operation S110, the temporal sequence of intraluminal images $140_{1 \ldots n}$ may be received via any form of data communication, including wired and wireless communication. By way of some examples, when wired communication is used, the communication may take place via an electrical or optical cable, and when wireless communication is used, the communication may for example be via RF or infrared signals. The intraluminal images $140_{1 \ldots n}$ may be received directly from the intraluminal imaging device 130, or indirectly, for example via a computer readable storage medium. Thus, the intraluminal images $140_{1 \ldots n}$ may represent live images that are generated instantaneously before being received, or they may be have been generated some seconds, minutes, hours, or even days, or a longer period, beforehand. The intraluminal images $140_{1 \ldots n}$ may be generated by an IVUS imaging device, or another intraluminal imaging device, as mentioned above. Each image in the temporal sequence of images may be referred to as an image frame.

The intraluminal images $140_{1 \ldots n}$ may be stored, for example in memory MEM illustrated in FIG. 3, or in a buffer (not illustrated in FIG. 3), prior to the operation of identifying S120, whether or not the first intraluminal image $140_{i \subset 1 \ldots n}$ represents a suitable end point location for the stent. The operation S120 may include displaying associated text, or an icon, or another identification on a display device, or generating an identification via another visual, or an audio alert.

Various additional operations may also be performed in combination with the above-described operations S110 and S120.

In general, the operation of identifying S120, whether or not the first intraluminal image $140_{i \subset 1 \ldots n}$ represents a suitable end point location for the stent, may be based on measurements of the lumen and/or the shape of the lumen, or a classification performed by an artificial intelligence algorithm.

As mentioned above, typically a physician will determine the stent's landing zone such that the stent overlaps a diseased region and the ends of the stent are located in healthy regions whilst preferably avoiding that the stent overlaps any confluences. Intraluminal images that represent healthy regions typically have a lumen area that is close to the average lumen area for a patient cohort. By contrast, intraluminal images that represent diseased regions often include compressions or thromboses where the lumen area is significantly less than the average lumen area for a patient cohort. Confluences occur where there is a branch from the lumen to an adjoining lumen. At a confluence, the lumen may bifurcate, or two lumens may merge into a single lumen. Intraluminal images that represent confluences typically have a lumen area that is significantly greater than the average lumen area for a patient cohort. It can be difficult to position a stent at a confluence without the risk of it moving over time. Thus, measurements of the lumen may be used to distinguish between healthy regions, diseased regions, and confluences, and thereby determine whether or not an intraluminal image represents a suitable end point location for the stent.

The shape of a lumen in intraluminal images may be used in a similar manner to distinguish between healthy regions, unhealthy regions, and confluences, and thereby determine whether or not an intraluminal image represents a suitable end point location for a stent. For example, healthy regions of the lumen may have a shape that is close to circular, whereas diseased regions such as compressions and thromboses may have an irregular, i.e. non-circular shape. The presence of irregular shapes such as an oval, or even sharp angles in a lumen are often indicative of a diseased region of the lumen. However, an irregular shape alone may be insufficient to diagnose a lumen as being unhealthy, particularly if the lumen area is not significantly lower than the average lumen area for a patient cohort. Thus, in some examples, a distinction between healthy and unhealthy regions may be made based on a combination of lumen shape, and lumen measurements, factors. At confluences, the shape of a healthy lumen may be circular within a major range of rotational angles about the lumen axis, and the shape of the lumen may bulge outwards within a minor range of rotational angles around the lumen axis where the lumen wall is defined by the wall of the adjoining lumen.

Measurements of the lumen area, and the shape may be obtained by segmenting the intraluminal images. Various image segmentation techniques are known for this purpose. The lumen measurements may for example include determining a maximum lumen width in the segmented intraluminal images and a corresponding width in an orthogonal direction. Other lumen dimensions, such as for example a difference or ratio between the measurements of the minor- and major-axis of the cross section of the lumen, may also be computed. The lumen measurements or shape may for example be determined by fitting a shape such as an ellipse to the lumen in the segmented intraluminal image.

The analysis of the intraluminal images to determine whether they represent a healthy or diseased region, or a confluence, and thus whether they represent a suitable end point location for a stent, may also include a weighting of one or more of the above lumen measurement, and lumen shape, factors.

Image classification techniques that use artificial intelligence algorithms may also be used to analyse the intraluminal images and thus determine whether they represent a suitable end point location for a stent. The intraluminal images may be segmented prior to their analysis by the artificial intelligence algorithm, or alternatively the intraluminal images may not be segmented beforehand. By way of an example, a neural network may be trained to classify intraluminal images as representing healthy regions, or diseased regions such as compressions and thromboses, or confluences. The neural network may alternatively be trained to classify intraluminal images directly as to whether or not they represent a suitable end point location for a stent. The neural network may be trained by inputting training data into the neural network that includes images that have been labelled with their suitability, or one of the aforementioned, and more specific, "ground truth" classifications, and optimising the parameters of the neural network based on the value of a loss function representing a difference between the classification that is predicted by the neural network, and the label.

Thus, the method illustrated in FIG. 2, may optionally follow the left-hand branch illustrated in FIG. 2, and include the operation of analysing S130 the temporal sequence of intraluminal images $140_{1\ldots n}$ by:

segmenting the intraluminal images $140_{1\ldots n}$, and comparing a measurement of the lumen 110 represented in the segmented intraluminal images with an expected measurement, and/or comparing a shape of the lumen 110 represented in the segmented intraluminal images with an expected shape; and/or classifying the intraluminal images $140_{1\ldots n}$ using an artificial intelligence algorithm; and wherein the identifying S120 is performed based on the analysing S130.

Since the analysing operation S130 is performed automatically in the above method, workflow is improved and/or a consistent analysis is provided by the method.

Figure 4:
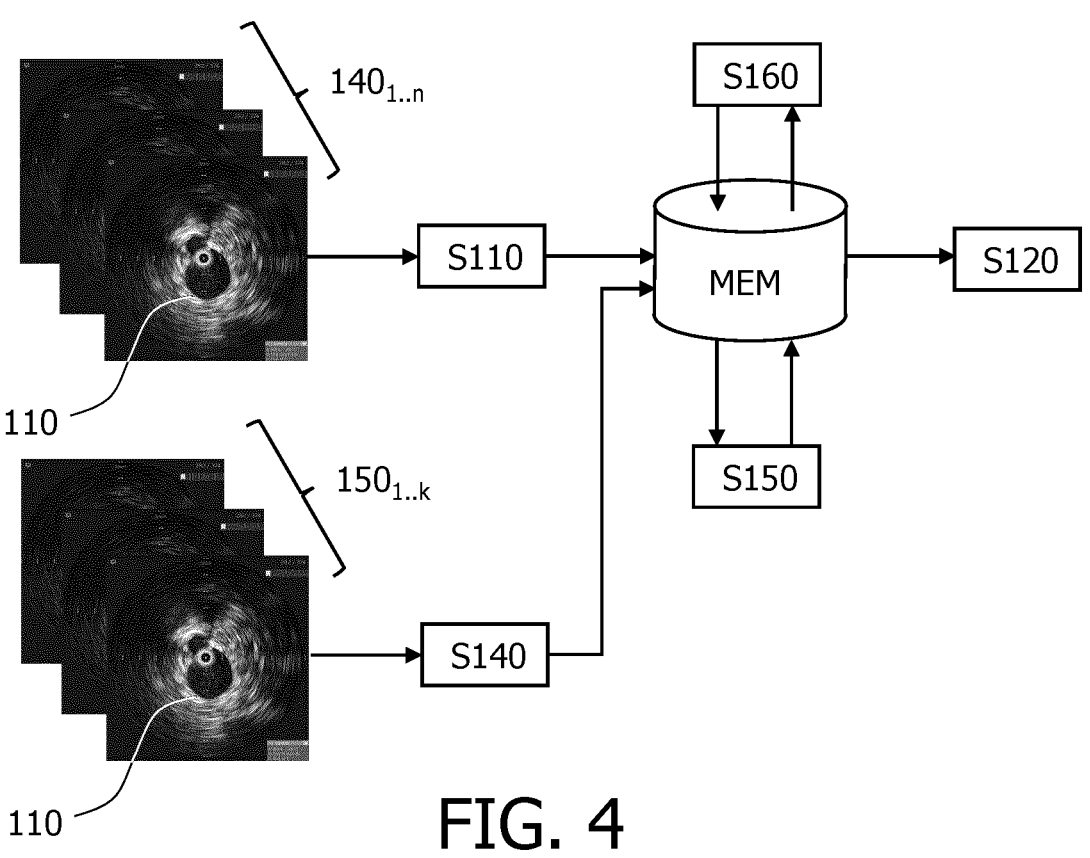
FIG. 4 is a schematic diagram illustrating an example of determining a suitability of positions along a lumen as end point locations for a stent, including analysing S150 a temporal sequence of pre-procedural intraluminal images $150_{1 \ldots k}$, in accordance with some aspects of the disclosure.

In an alternative implementation, the method follows the right-hand branch illustrated in FIG. 2. This implementation is illustrated with reference to FIG. 4, which is a schematic diagram illustrating an example of determining a suitability of positions along a lumen as end point locations for a stent. It includes analysing S150 a temporal sequence of pre-procedural intraluminal images $150_{1\ldots k}$, in accordance with some aspects of the disclosure. In this implementation the intraluminal images $140_{1\ldots n}$ that are respectively received and identified in the operations S110 and S120 described above, represent intra-procedural images, and further operations are carried out by the one or more processors:

receiving S140, from the intraluminal imaging device 130, a temporal sequence of pre-procedural intraluminal images $150_{1\ldots k}$ representing the lumen 110;

analysing S150 the temporal sequence of pre-procedural intraluminal images $150_{1\ldots k}$ to determine whether the pre-procedural intraluminal images represent suitable end point locations for the stent; and comparing S160 the first intra-procedural intraluminal image $140_{i\subset1\ldots n}$ with the pre-procedural intraluminal images $150_{1\ldots k}$ to identify a matching pre-procedural intraluminal image $150_{j\subset1\ldots k}$; and wherein the identifying S120 is based on a result of the analysing S150 for the matching pre-procedural intraluminal image $150_{j\subset1\ldots k}$.

In this implementation the analysing operation S150 is also performed automatically. In this implementation, the pre-procedural intraluminal images $150_{1\ldots k}$ are generated earlier in time than the intra-procedural images $140_{1\ldots n}$. For example, the pre-procedural intraluminal images $150_{1\ldots k}$ may generated in a pre-procedural IVUS pullback procedure, and the intra-procedural images $140_{1\ldots n}$ generated during a subsequent IVUS imaging procedure in which the physician re-visits sites that are considered to be interesting from the pre-procedural IVUS pullback procedure. Performing the analysis on the pre-procedural images in this manner alleviates the processing burden of determining suitable end point locations for the stent because this processing operation may take place in the period between generating the pre-procedural and intra-procedural images.

Various metrics may be used in the operation of comparing S160 the first intraluminal image $140_{i\subset1\ldots n}$ with the pre-procedural intraluminal images $150_{1\ldots k}$ to identify a matching pre-procedural intraluminal image $150_{j\subset1\ldots k}$. For example, the value of a least squares error function may be computed based on a difference in their image intensities after registering the images to one another. Alternatively, a learned similarity metric may be used. Temporal constraints may also be applied in order to ensure that matching images in the sequences of pre-procedural and intra-procedural images are coherent in the direction of the pullback.

The operation of analysing S150 the temporal sequence of pre-procedural intraluminal images $150_{1\ldots k}$ to determine whether the pre-procedural intraluminal images represent suitable end point locations for the stent, may be performed in a similar manner to that described above in relation to the analysing performed in the operation S130. Thus, analysing S150 the temporal sequence of pre-procedural intraluminal images $150_{1\ldots k}$, may include:

segmenting the pre-procedural intraluminal images $150_{1\ldots k}$, and comparing a measurement of the lumen 110 represented in the segmented pre-procedural intraluminal images with an expected measurement, and/or comparing a shape of the lumen represented in the segmented pre-procedural intraluminal images with an expected shape; and/or classifying the pre-procedural intraluminal images $150_{1\ldots k}$ using an artificial intelligence algorithm.

As described above, the analysing performed in the operation S150 may include: determining whether or not the pre-procedural intraluminal images $150_{1\ldots k}$ represent at least one of: a healthy region of the lumen 110, a confluence in the lumen 110, a compression in the lumen 110, and a thrombosis in the lumen 110.

In one example, the comparison between the first intraluminal image $140_{i\subset1\ldots n}$, and the pre-procedural intraluminal images $150_{1\ldots k}$, that is made in the operation S160, may be improved by basing the comparison on the image under consideration as well as its neighbouring images. In this example, the operation of comparing S160 the first intra-procedural intraluminal image $140_{i\subset1\ldots n}$ with the pre-procedural intraluminal images $150_{1\ldots k}$ to identify a matching pre-procedural intraluminal image $150_{j\subset1\ldots k}$, further comprises:

comparing one or more neighbouring intraluminal images of the first intra-procedural intraluminal image $140_{i\subset1\ldots n}$ with one or more corresponding neighbouring images from the pre-procedural intraluminal images $150_{1\ldots k}$, to determine whether a match exists.

This has the effect of enforcing temporal consistency between the stream of intra-procedural images and the pre-procedural images.

In one example, the result of analysing S150 the temporal sequence of pre-procedural intraluminal images $150_{1\ldots k}$ may also be displayed. This allows a physician to determine which sites along the lumen may be worthwhile to re-visit with the intraluminal imaging device in order to confirm the position as being suitable for a stent. The result of the analysing may be displayed in various ways. For example, the result may be displayed as a longitudinal view of the pre-procedural intra-luminal images $150_{1\ldots k}$ along the axis of the lumen, and by including a marker or a colour coding indicative of the suitability, or otherwise, of each position along the lumen as an end point location for a stent. In another example, an X-ray image may be displayed that includes the position along the lumen 110 represented by the first intraluminal image $140_{i\subset1\ldots n}$.

In another example, intraluminal images are generated at different positions along the lumen, and the positions of the intraluminal images are indicated in a common X-ray image. The anatomical information provided by the common X-ray image may be useful in confirming the positions as being suitable for a stent. In this example, X-ray images are generated contemporaneously with the intraluminal images, and a mapping operation is performed wherein the position of one of the intraluminal images along the lumen, is mapped from one of the X-ray images to a corresponding position in another X-ray image.

This example is illustrated with reference to FIG. 5, which is a schematic diagram illustrating a first X-ray image 180 and a second X-ray image 190 that are generated contemporaneously with a first intraluminal image 140; and a second intraluminal image $140_m$, respectively, in accordance with some aspects of the disclosure. The X-ray images 180, 190 illustrated in FIG. 5 include the intraluminal imaging catheter at respective first and second positions 160, 170 along a vascular lumen 110. The X-ray images 180, 190 may include dense structures such as bone that act as landmarks (not illustrated in FIG. 5). However, the vascular lumen 110 is almost invisible in X-ray images owing to the small difference in X-ray attenuation values between lumen tissue and water. The vascular lumen 110 is therefore illustrated in FIG. 5 with a dashed outline. The first and second positions 160, 170 may correspond to positions of the intravascular imaging catheter along the lumen during an intraluminal imaging catheter pullback procedure. The positions may alternatively correspond to positions of the intravascular imaging catheter that the physician has guided the intraluminal imaging catheter to in the lumen, and which the physician considers to be suitable for positioning the end of a stent. The mapping operation is illustrated in FIG. 5 by way of the dashed horizontal line indicating a mapping of the position 170 of the second intraluminal image $140_m$ from the lumen in the second X-ray image 190, to a corresponding position in the first X-ray image 180.

Figure 5:
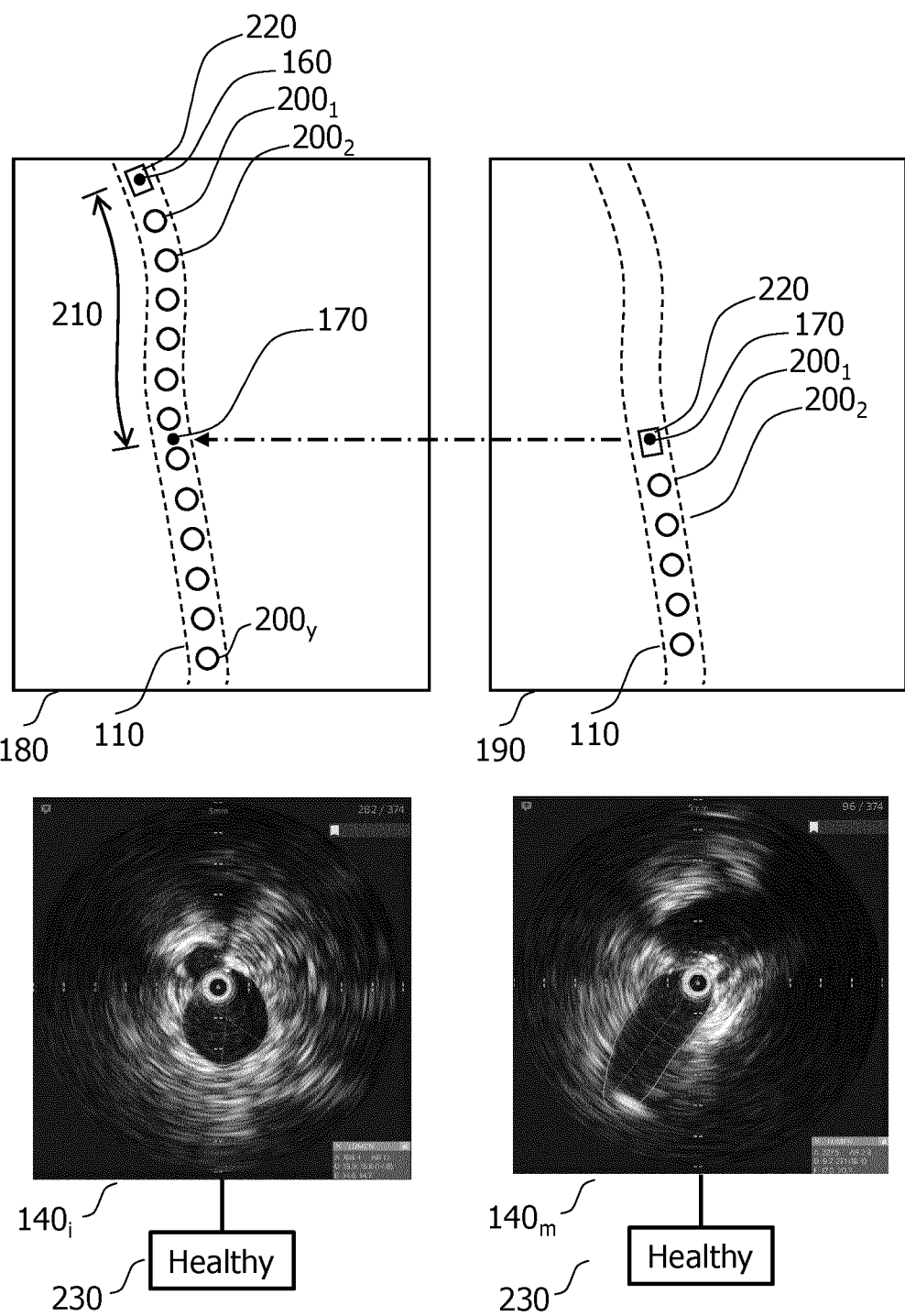
FIG. 5 is a schematic diagram illustrating a first X-ray image 180 and a second X-ray image 190 that are generated contemporaneously with a first intraluminal image $140_i$ and a second intraluminal image $140_m$, respectively, in accordance with some aspects of the disclosure.
Figure 6:
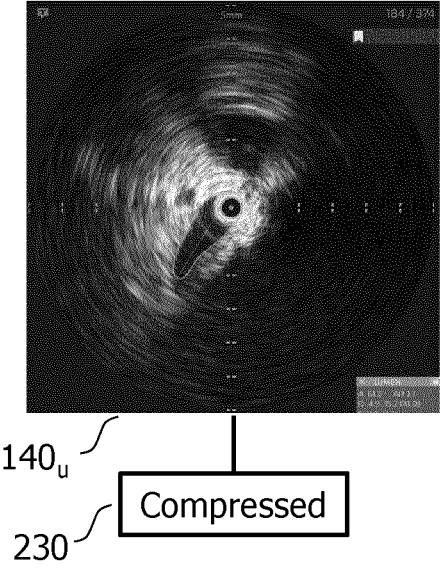
FIG. 6 illustrates an intraluminal IVUS image $140_u$ of an unhealthy, or "compressed" lumen, and in which the lumen area is significantly reduced as compared to the average lumen area for a similar patient cohort.

In the example illustrated in FIG. 5, the illustrated intraluminal images $140_i$ and $140_m$ both represent IVUS images of healthy regions of the lumen. The healthy lumen represented in intraluminal image 140; has a circular shape, as represented by the dark central region in the image. In spite of its more oval-shape, the lumen represented in the intraluminal image $140_m$ is still considered to be healthy since its area is not significantly reduced as compared to the average lumen area for a similar patient cohort. By way of a comparison, FIG. 6 illustrates an intraluminal IVUS image $140u$ of an unhealthy, or "compressed" lumen, and in which the lumen area is significantly reduced as compared to the average lumen area for a similar patient cohort.

In the example illustrated in FIG. 5, in addition to the receiving and identifying operations S110 and S120 described above with reference to FIG. 2, the first intraluminal image $140_{i \subset 1 \ldots n}$ represents a first position 160 along the lumen 110; and the operation of receiving S110 a temporal sequence of intraluminal images $140_{1 \ldots n}$, comprises receiving a second intraluminal image $140_{m \subset 1 \ldots n}$ representing a second position 170 along the lumen 110. The method also includes:

receiving a first X-ray image 180, and a second X-ray image 190, the first X-ray image and the second X-ray image being generated contemporaneously with the first intraluminal image $140_{i \subset 1 \ldots n}$ and the second intraluminal image $140_{m \subset 1 \ldots n}$, respectively;

determining the positions 160, 170 of the first and second intraluminal images $140_{i \subset 1 \ldots n}$, $140_{m \subset 1 \ldots n}$ in the respective first and second X-ray images 180, 190; and mapping one of the determined positions 160, 170 of the first and second intraluminal images $140_{i \subset 1 \ldots n}$, $140_{m \subset 1 \ldots n}$, from the respective first or second X-ray image 180, 190, to the other of the first and second X-ray images 180, 190.

In this example, the X-ray images 180, 190 may be received by any means of data communication, as was described above in relation to the temporal sequence of intraluminal images $140_{1 \ldots n}$. The X-ray images 180, 190 may be generated contemporaneously by synchronising the timing of their generation with the generation of the intraluminal images $140_{1 \ldots n}$ by the intraluminal imaging system. Alternatively, contemporaneous X-ray and intraluminal images may be provided by selecting an X-ray or intraluminal image from a stream of images provide a contemporaneously-generated image that is generated closest in time to the respective intraluminal or X-ray image. In one example, the first and second intraluminal images $140_{i \subset 1 \ldots n}$, $140_{m \subset 1 \ldots n}$ are selected automatically from the temporal sequence of intraluminal images $140_{1 \ldots n}$ in response to a generation of the first and second X-ray images 180, 190, respectively.

Various techniques may be used in the operation of mapping one of the determined positions 160, 170 of the first and second intraluminal images $140_{i \subset 1 \ldots n}$, $140_{m \subset 1 \ldots n}$, from the respective first or second X-ray image 180, 190, to the other of the first and second X-ray images 180, 190. In one example, the first and second X-ray images 180, 190 may be overlaid in order to map the position from one X-ray image to the other X-ray image. In another example, the mapping includes:

performing an image-based registration between the first and second X-ray images 180, 190;

computing a spatial transform between corresponding image features in the first and second X-ray images 180, 190 based on the image-based registration; and wherein the mapping is performed based on the computed spatial transform.

Performing the aforementioned image-based registration advantageously compensates for any motion between the generation of the first and second X-ray images 180, 190, thereby improving the accuracy of the mapped position.

In general, the positions 160, 170 of the intraluminal images along the lumen may be determined based on a detection of the imaging portion 220, or another portion, of the intraluminal imaging device, in the X-ray images 180, 190. The imaging portion 220 typically includes a radiopaque material that is visible in the X-ray images. By detecting the imaging portion 220, the relative position of the imaged region of the lumen that is imaged in the intraluminal images, may be determined based on the known field of view of the intraluminal imaging device. For example, some IVUS imaging catheters typically have a field of view that is circumferentially around the longitudinal axis of the IVUS imaging catheter, and also in a normal direction with respect to its imaging portion 220. Other IVUS imaging catheters have a field of view that is circumferentially around the longitudinal axis of the IVUS imaging catheter, and also tilted in a forward-looking direction, with respect to the imaging portion 220. The position along the lumen that corresponds to the intraluminal image, may therefore be determined based on a knowledge of the position of the detected imaging portion and the known imaging field of view.

One or more fiducial markers may also be disposed on the intraluminal imaging device. Fiducial markers include a radiopaque material that may be detected in the X-ray images. The relative position of the imaged region of the lumen may therefore be determined based on the detected position of the radiopaque marker(s) in a similar manner.

Various techniques may be used in the operation of determining the positions $160$, $170$ of the intraluminal images in the respective X-ray images $180$, $190$. For example, the use of computer vision object detection techniques, image segmentation techniques, and an artificial intelligence algorithm, are contemplated. By way of an example, when an artificial intelligence algorithm is used, the artificial intelligence algorithm may be provided by a neural network that is trained to identify the position of the imaging portion $220$ of the intraluminal imaging catheter in the X-ray images. The neural network may be trained to identify the position by inputting into the neural network, X-ray image training data that includes the ground truth position of the imaging portion $220$, and adjusting parameters of the neural network using a loss function representing a difference between the predicted position of the imaging portion $220$ that is predicted by the neural network, and its ground truth position from the X-ray image training data. The ground truth position may be identified in the X-ray image training data by an expert. Suitable types of neural networks for this purpose include a U-Net, a UNet++, a VNet, a convolutional neural network "CNN", and a region-based CNN "RCNN", and so forth.

Thus, the operation of determining the positions of the first and second intraluminal images $140_{i \subset 1 \ldots n}$, $140_{m \subset 1 \ldots n}$ in the respective first and second X-ray images $180$, $190$, may include detecting the position of an imaging portion $220$ of the intraluminal imaging device $130$ in the respective first and second X-ray images $180$, $190$ by:

executing a computer vision object detection technique; and/or segmenting the first and second X-ray images $180$, $190$; and/or applying an artificial intelligence algorithm trained to detect the imaging portion $220$ of the intraluminal imaging device $130$, to the respective first and second X-ray images $180$, $190$.

The method or operations that are carried out by the one or more processors may optionally also include offsetting the detected position $160$, $170$ of the imaging portion $220$ along the lumen $110$ by a predetermined distance representing a difference in position between the imaging portion $220$ of the intraluminal imaging device and an imaged region of the lumen $110$ imaged by the intraluminal imaging device $130$. In so doing, an accurate position of the intraluminal images may be determined in the X-ray images.

As mentioned above, having determined a stent's landing zone, the physician typically measures a length of the landing zone in order to specify a length of a stent for insertion into the lumen. In one example, the method also includes determining a length $210$ of a portion of the lumen between the positions $160$, $170$ of the first and second intraluminal images $140_{i \subset 1 \ldots n}$, $140_{m \subset 1 \ldots n}$. In this example, the intraluminal imaging device $130$ includes a plurality of fiducial markers $200_{1 \ldots y}$ disposed axially along a length of the device $130$, and the mapping is performed such that the X-ray image $180$, $190$ into which the position $160$, $170$ is mapped includes one or more of the fiducial markers $200_{1 \ldots y}$ between the positions $160$, $170$ of the first and second intraluminal images $140_{i \subset 1 \ldots n}$, $140_{m \subset 1 \ldots n}$; and the method further includes:

computing a length $210$ of a portion of the lumen $110$ between the positions $160$, $170$ of the first and second intraluminal images $140_{i \subset 1 \ldots n}$, $140_{m \subset 1 \ldots n}$ based on

12 a count of the number of fiducial markers between the positions $160$, $170$ of the first and second intraluminal images $140_{i \subset 1 \ldots n}$, $140_{m \subset 1 \ldots n}$ in the X-ray image $180$, $190$ into which the position is mapped.

This example is illustrated with reference to FIG. $5$. The fiducial markers $200_{1 \ldots y}$ that are disposed axially along a length of the intraluminal imaging device include a radiopaque material such as stainless steel, gold, platinum, and so forth, and are therefore detectable in the X-ray images $180$, $190$. Advantageously, in this example, the fiducial markers are inherently present in one of the X-ray images, and so there is no need to re-position the intraluminal imaging device in the X-ray images in order to perform the length measurement. Moreover, the positions of the fiducial markers that are used in the length measurement are inherently registered to one end of the portion of the lumen that is to be measured, simplifying the measurement. The computed length $210$ of the portion of the lumen $110$ may correspond to a recommended length of a stent for insertion into the lumen $110$.

The fiducial markers may be detected in the X-ray image using image analysis techniques. Such techniques are known from the field of computer vision. A path computation method such as front propagation or fast marching may be used to determine the order of the fiducial markers. Since the count is performed automatically in the method, it eases workflow and/or avoids counting errors since manual counting by the physician is unnecessary. Manually counting the fiducial markers is prone to errors because of the long length of diseased lumens that are treated in deep venous interventional procedures. In such procedures the length of diseased lumens may exceed fifteen centimetres or more.

In practice, the length $210$ of the lumen $110$ that is to be measured, might not correspond to an integer number of fiducial markers. In this situation, interpolation may be used to more accurately determine the length $210$ of the portion of the lumen $110$. Thus, in some examples, the operation of computing a length $210$ of a portion of the lumen $110$ may include:

interpolating a distance between one or more of the fiducial markers $200_{1 \ldots y}$ and the first position $160$ and/or the second position $170$.

In one example, the intraluminal images $140_{1 \ldots n}$ illustrated in FIG. $5$ represent intra-procedural images of the lumen, and the method also includes receiving pre-procedural images of the lumen. In this example, and in a similar manner to that described above in relation to FIG. $4$, the pre-procedural images are analysed to determine whether images in the pre-procedural images represent suitable end point locations for a stent, and determining the suitability of the intra-procedural images as end point locations for a stent involves comparing the intra-procedural images with the preprocedural images. With reference to FIG. $5$, in this example, the intraluminal images $140_{1 \ldots n}$ represent intra-procedural images, and the method further comprises:

receiving S140, from the intraluminal imaging device $130$, a temporal sequence of pre-procedural intraluminal images $150_{1 \ldots k}$ representing the lumen $110$;

analysing S150 the temporal sequence of pre-procedural intraluminal images $150_{1 \ldots k}$ to determine whether the pre-procedural intraluminal images represent suitable end point locations for the stent;

comparing the first and second intra-procedural intraluminal images $140_{i \subset 1 \ldots n}$, $140_{m \subset 1 \ldots n}$ with the pre-procedural intraluminal images $150_{1 \ldots k}$ to identify respective first and second matching pre-procedural intraluminal images;

and wherein the identifying S120 comprises identifying whether or not the first and second intra-procedural intraluminal images $140_{i \subset 1 \ldots n}$, $140_{m \subset 1 \ldots n}$ represent suitable end point locations for the stent, based on a result of the analysing S150 for the first and second matching pre-procedural intraluminal images, and displaying the result 230 of the analysing S150 for the first and/or second matching pre-procedural intraluminal images.

The result 230 of the analysing S150 may be displayed by, for example, providing a text label on a display, as illustrated in FIG. 5 and FIG. 6 via the example labels Healthy and Compressed, or displayed in another manner. For example, the result may be displayed by means of an icon, or highlighting the position in the X-ray image 180, 190 with a colour or intensity that is indicative of the suitability, or otherwise, of the position as and end point location for a stent. In another example, a marker may be provided in the X-ray image 180 that includes the mapped positions. The marker may highlight a region of the X-ray image with a colour, or intensity, or a line or a symbol that indicates indicate result of the analysis, i.e. "Healthy", or "Confluence", or "Compression", or "Thrombosis".

As mentioned above, performing the analysis on the pre-procedural images in this manner alleviates the processing burden of determining suitable end point locations for the stent because this processing may take place in the time interval between the generation of the pre-procedural images and the intra-procedural images.

This example may also include an operation of receiving user input confirming the positions 160, 170 along the lumen 110 as representing suitable end point locations for the stent. This gives the physician an opportunity to confirm the suitability and/or select an alternative position as an end point location for the stent. In accordance with this example, the method further includes:

receiving user input confirming the first and second positions 160, 170 along the lumen 110 as representing suitable end point locations for the stent; and wherein the computing a length 210 of a portion of the lumen 110, is performed automatically and contingent on the receiving user input confirming the first and second positions 160, 170 along the lumen 110 as representing suitable end point locations for the stent.

Any of the aforementioned methods, may also include displaying one or more of the following:

the first and/or second intraluminal image $140_{i \subset 1 \ldots n}$, $140_{m \subset 1 \ldots n}$;

the result 230 of the analysing the temporal sequence of pre-procedural intraluminal images $150_{1 \ldots k}$;

the result of the analysing for the matching pre-procedural intraluminal image;

the result of the analysing for the first and/or second matching pre-procedural intraluminal image;

the first and/or second X-ray image 180, 190;

the computed length 120 of the portion of the lumen 110.

The above-described methods may be incorporated into a clinical procedure in different ways, as illustrated by the examples above. It is noted that each of these examples may be preceded by an initial X-ray imaging procedure that uses a contrast agent to provide a map of the vasculature. This initial procedure, for example a venogram, may include the use of a digital subtraction angiography "DSA" technique.

The above examples are to be understood as illustrative of the present disclosure, and not restrictive. Further examples are also contemplated. For instance, the example methods described in relation to the system 100, may also be provided as a computer-implemented method, a computer program product, or by a computer-readable storage medium, in a corresponding manner. It is to be understood that a feature described in relation to any one example may be used alone, or in combination with other described features, and may be used in combination with one or more features of another of the examples, or a combination of other examples. Furthermore, equivalents and modifications not described above may also be employed without departing from the scope of the invention, which is defined in the accompanying claims.

In the claims, the word "comprising" does not exclude other elements or operations, and the indefinite article "a" or "an" does not exclude a plurality. The mere fact that certain features are recited in mutually different dependent claims does not indicate that a combination of these features cannot be used to advantage. Any reference signs in the claims should not be construed as limiting their scope.

The invention claimed is:

1. A system for determining a suitability of positions along a lumen as end point locations for a stent, the system comprising at least one processor configured to:

receive, from an intraluminal imaging device, a temporal sequence of intraluminal images representing the positions along the lumen, wherein the temporal sequence of intraluminal images includes at least a first intraluminal image;

analyse the temporal sequence of intraluminal images using an artificial intelligence algorithm; and identify whether or not the first intraluminal image represents a suitable end point location for the stent based on the analysing.

2. The system according to claim 1, wherein the temporal sequence of intraluminal images represent intra-procedural images, and wherein the at least one processor is configured to:

receive, from the intraluminal imaging device, a temporal sequence of pre-procedural intraluminal images representing the lumen;

analyse the temporal sequence of pre-procedural intraluminal images to determine whether the temporal sequence of pre-procedural intraluminal images represent one or more suitable end point locations for the stent; and compare the first intraluminal image with the temporal sequence of pre-procedural intraluminal images to identify a matching pre-procedural intraluminal image, and wherein the identifying whether or not the first intraluminal image represents the suitable end point location is based on the matching pre-procedural intraluminal image.

3. The system according to claim 2, wherein the comparing the first intraluminal image with the temporal sequence of pre-procedural intraluminal images to identify the matching pre-procedural intraluminal image comprises:

comparing one or more neighbouring intraluminal images of the first intraluminal image with one or more corresponding neighbouring images from the temporal sequence of pre-procedural intraluminal images to determine whether a match exists.

4. The system according to claim 1, wherein the analysing the temporal sequence of intraluminal images comprises:

segmenting the temporal sequence of intraluminal images; and comparing a measurement of the lumen represented in the segmented temporal sequence of intraluminal images with an expected measurement and/or comparing a shape of the lumen represented in the segmented temporal sequence of intraluminal images with an expected shape.

5. The system according to claim 1, wherein the analysing the temporal sequence of intraluminal images comprises:

determining whether or not the temporal sequence of intraluminal images represent at least one of: a healthy region of the lumen, a confluence in the lumen, a compression in the lumen, or a thrombosis in the lumen.

6. The system according to claim 1, wherein the at least one processor is further configured to:

output, to a display, a result of the analysing the temporal sequence of intraluminal images; and/or output, to the display, an X-ray image including a position along the lumen represented by the first intraluminal image.

7. A system for determining a suitability of positions along a lumen as end point locations for a stent, the system comprising at least one processor configured to:

receive, from an intraluminal imaging device, a temporal sequence of intraluminal images representing the positions along the lumen, wherein the temporal sequence of intraluminal images includes at least a first intraluminal image representing a first position along the lumen and a second intraluminal image representing a second position along the lumen;

receive a first X-ray image and a second X-ray image, the first X-ray image and the second X-ray image being generated contemporaneously with the first intraluminal image and the second intraluminal image, respectively; and identify whether or not the first intraluminal image and the second intraluminal image represent suitable end point locations for the stent.

8. The system according to claim 7, wherein the at least one processor is further configured to:

determine the first position of the first intraluminal image in the first X-ray image and the second position of the second intraluminal image in the second X-ray image.

9. The system according to claim 8, wherein the at least one processor is further configured to:

perform a mapping of the first position of the first intraluminal image from the first X-ray image to the second X-ray image; and/or perform the mapping of the second position of the second intraluminal image from the second X-ray image to the first X-ray image.

10. The system according to claim 9, wherein the intraluminal imaging device further comprises a plurality of fiducial markers disposed axially along a length of the device, wherein the first X-ray image, when the mapping of the second position is performed, or the second X-ray image, when the mapping of the first position is performed, includes one or more of the plurality of fiducial markers between the first and second positions of the first and second intraluminal images, respectively; and wherein the at least one processor is further configured to:

compute a length of a portion of the lumen between the first and second positions of the first and second intraluminal images, respectively, based on a count of the one or more of the plurality of fiducial markers between the first and second positions in the first X-ray image, when the mapping of the second position is performed, or the second X-ray image, when the mapping of the first position is performed.

11. The system according to claim 10, wherein the at least one processor is further configured to receive user input confirming the first and second positions along the lumen as representing the suitable end point locations for the stent, and wherein the computing the length of the portion of the lumen is performed automatically and contingent on the receiving the user input.

12. The system according to claim 10, wherein the at least one processor is further configured to output, to a display, the computed length of the portion of the lumen.

13. The system according to claim 9, wherein the mapping comprises:

performing an image-based registration between the first and second X-ray images;

computing a spatial transform between corresponding image features in the first and second X-ray images based on the image-based registration, and wherein the mapping is performed based on the computed spatial transform.

14. The system according to claim 8, wherein the determining the first position of the first intraluminal image in the first X-ray image and the second position of the second intraluminal image in the second X-ray image comprises detecting a position of an imaging portion of the intraluminal imaging device by:

executing a computer vision object detection technique;

segmenting the first and second X-ray images; and/or applying an artificial intelligence algorithm trained to detect the imaging portion of the intraluminal imaging device, to the first and second X-ray images.

15. The system according to claim 14, wherein the determining the first position of the first intraluminal image in the first X-ray image and the second position of the second intraluminal image in the second X-ray image comprises:

offsetting the detected position of the imaging portion along the lumen by a predetermined distance representing a difference in the position between the imaging portion and a region of the lumen imaged by the intraluminal imaging device.

16. The system according to claim 7, wherein the first and second intraluminal images are selected automatically from the temporal sequence of intraluminal images in response to a generation of the first and second X-ray images, respectively.

17. The system according to claim 7, wherein the temporal sequence of intraluminal images represent intra-procedural images, and wherein the at least one processor is further configured to:

receive, from the intraluminal imaging device, a temporal sequence of pre-procedural intraluminal images representing the lumen;

analyse the temporal sequence of pre-procedural intraluminal images to determine whether the temporal sequence of pre-procedural intraluminal images represent one or more suitable end point locations for the stent;

compare the first and second intraluminal images with the temporal sequence of pre-procedural intraluminal images to identify respective first and second matching pre-procedural intraluminal images, wherein the identifying whether or not the first intraluminal image and the second intraluminal image represent the suitable end point locations is based on the first and second matching pre-procedural intraluminal images.

18. The system according to claim 17, wherein the at least one processor is further configured to output, to a display, at least one of:

the first and/or second intraluminal image; or the first and/or second X-ray image.

19. The system according to claim 17, wherein the at least one processor is further configured to output, to a display, at least one of:

a result of the analysing the temporal sequence of pre-procedural intraluminal images; or a result of the identifying the first and/or second matching pre-procedural intraluminal images.

\* \* \* \* \*